(12) United States Patent
Punnoose et al.

(10) Patent No.: US 8,187,638 B2
(45) Date of Patent: *May 29, 2012

(54) PREFERENTIAL KILLING OF CANCER CELLS AND ACTIVATED HUMAN T CELLS USING ZNO NANOPARTICLES

(75) Inventors: Alex Punnoose, Boise, ID (US); Madhusudan R. Kongara, Boise, ID (US); Denise Wingett, Boise, ID (US)

(73) Assignee: Boise State University, Boise, ID (US)

( * ) Notice: Subject to any disclaimer, the term of this patent is extended or adjusted under 35 U.S.C. 154(b) by 280 days.

This patent is subject to a terminal disclaimer.

(21) Appl. No.: 12/235,415

(22) Filed: Sep. 22, 2008

(65) Prior Publication Data

US 2009/0136580 A1 May 28, 2009

Related U.S. Application Data (60) Provisional application No. 60/974,460, filed on Sep. 22, 2007.

(51) Int. Cl.
*A61K 9/14* (2006.01)
*A61K 33/08* (2006.01)
*A61K 33/30* (2006.01)
(52) U.S. Cl. ...... 424/489; 424/490; 424/1.33; 424/1.61; 424/155.1; 424/641; 514/494
(58) Field of Classification Search .......... 424/489, 424/490, 1.33, 1.61, 155.1, 641; 514/494
See application file for complete search history.

(56) References Cited

U.S. PATENT DOCUMENTS

| 6,165,440 A * | 12/2000 | Esenaliev ............ 424/1.11 |
| 2004/0062817 A1* | 4/2004 | Peshoff ............ 424/642 |
| 2007/0015226 A1* | 1/2007 | Hirai et al. ............ 435/7.23 |
| 2008/0317768 A1* | 12/2008 | Bianchi ............ 424/179.1 |
| 2009/0137666 A1* | 5/2009 | Wang et al. ............ 514/494 |

FOREIGN PATENT DOCUMENTS

| WO | WO 2009/039508 | 3/2009 |
| WO | WO 2009/079056 | 6/2009 |

OTHER PUBLICATIONS

Ciardiello et al, EGFR antagonists in cancer treatment, The new england journal of medicine, pp. 1160-1174, Mar. 13, 2008.*
International Search Report, PCT/US2008/077284, Sep. 1, 2009 Applicant: Boise State University.
Wang, Wingett, Engelard, Feris, Reddy, Turner, Layne, Hanley, Bell, Tenne, Wang, Punnoose, "Fluorescent dye encapsulated ZnO particles with cell-specific toxicity for potential use in biomedical applications", Journal of Material Science: Materials in Medicine (2009) 20:11-22, U.S., published online Jul. 24, 2008.
Hays, Reddy, Graces, Engelhard, Shutthanandan, Luo, Xu, Giles, Wang, Thevuthasa, Punnoose, "Effect of Co doping on the structural, optical and magnetic properties of ZnO nanoparticles", Apr. 27, 2007, Journal of Physics: Condensed Matter (2007) 266203 (24pp), UK, published Jun. 7, 2007.
Reddy, Feris, Wingett, Hanley, Punnoose, "Selective toxicity of zinc oxide nanoparticles to prokaryotic and eukaryotic systems", Applied Physics Letters, May 24, 2007, 90, 213902, U.S.
Hagadone, Zach, "Nano cells on the attack: BSU researchers find cancer-killing particles", Sep. 8, 2008.
International Preliminary Report on Patentability, PCT/US2008/077252, Appilicant: Boise State University.

* cited by examiner

*Primary Examiner* — Mina Haghighatian
(74) *Attorney, Agent, or Firm* — McDermott Will & Emery LLP (57) ABSTRACT

Here we disclose the response of normal human cells to ZnO nanoparticles under different signaling environments and compare it to the response of cancerous cells. ZnO nanoparticles exhibit a strong preferential ability to kill cancerous T cells (~28-35X) compared to normal cells. Interestingly, the activation state of the cell contributes toward nanoparticle toxicity as resting T cells display a relative resistance while cells stimulated through the T cell receptor and CD28 costimulatory pathway show greater toxicity in direct relation to the level of activation. The novel findings of cell selective toxicity towards potential disease causing cells indicate a potential utility of ZnO nanoparticle in the treatment of cancer and/or autoimmunity.

21 Claims, 9 Drawing Sheets

PREFERENTIAL KILLING OF CANCER CELLS AND ACTIVATED HUMAN T CELLS USING ZNO NANOPARTICLES

This application claims priority of Provisional Application Ser. No. 60/974,460, filed Sep. 22, 2007, and entitled "Preferential Killing of Cancer Cells and Activated Human T Cells Using the Selective Toxicity of Zinc Oxide," which is hereby incorporated by reference.

This research was supported in part by Mountain States Tumor and Medical Research Institute, Boise, Id., NSF-Idaho-EPSCoR Program (EPS-0447689), DoE-EPSCoR grant (DE-FG02-04ER46142), NSF grants (DMR-0449639, MRI 0521315), and NIH (1R15 AI06277-01A1). We thank Dr. James Belthoff for his gracious assistance with statistical analysis.

BACKGROUND OF THE INVENTION

1. Field of the Invention

This invention relates generally to a new method for preferentially killing cancer and activated T cells with zinc oxide (ZnO) nanoparticles. More specifically, this invention relates to autoimmune disease and cancer treatment in humans and animals by preferentially killing cancer and activated T cells with relatively little damage to normal cells.

2. Background Art

The integration of nanotecluology and biology provides the opportunity for the development of new materials in the nanometer size range that may be applied to many potential applications in biological science and clinical medicine. When reduced to the nanoscale realm, unique size-dependent properties of nanomaterials, including nanopaiticles (NP), are manifested. The principal factors believed to cause properties of nanomaterials to differ from their bulk counterparts include an increase in relative surface area and quantum effects, which can affect chemical reactivity and other physical and chemical properties. For example, a particle of 30 nm size has 5% of it atoms on its surface compared to 50% of the atoms on the surface of a 3 nm particle. The altered properties of NP, and their similarity in size compared to naturally occurring biological structures, can allow them to readily interact with biomolecules on both the cell surface and within the cell and potentially affect cellular responses in a dynamic and selective manner. Materials that exploit these characteristics are becoming increasingly attractive for use in novel biomedical applications.

Although our understanding of the functioning of the human body at the molecular and nanometer scale has improved tremendously, advances in therapeutic options for treating severe and debilitating diseases such as cancer and autoimmunity have lagged by comparison. In this regard, nanomedicine, which is the application of nanotechnology to medical problems, can offer new approaches. With regards to cancer treatment, most current anticancer regimes do not effectively differentiate between cancerous and normal cells. This indiscriminate action frequently leads to systemic toxicity and debilitating adverse effects in normal body tissues including bone marrow suppression, neurotoxicity, and cardiomyopathy. Nanotechnology and nanomedicine can offer a more targeted approach which promises significant improvements in the treatment of cancer. In this study we have employed 8 nm zinc oxide (ZnO) NP in which the synthesis and properties have been previously described (Reddy K M, Feris K, Bell J, Wingett D G, Hanley C, Punnoose A 2007 Selective toxicity of zinc oxide nanoparticles to prokaryotic and eukalyotic systems *Applied Physics Letters* 90 213902-213903). The aim of the study was to investigate whether ZnO NP induce toxicity in a cell-specific manner, determine the mechanism(s) of toxicity, and whether these NPs have potential utility in novel biomedical applications seeking to eliminate pathogenic cells while sparing healthy body tissues.

SUMMARY OF INVENTION

Nanoparticles are increasingly being recognized for their potential utility in biological applications including nanomedicine. Here we examine the response of normal human cells to ZnO nanoparticles under different signaling environments and compare it to the response of cancerous cells. ZnO nanoparticles exhibit a strong preferential ability to kill cancerous T cells (~28-35X) compared to normal cells. Interestingly, the activation state of the cell contributes toward nanoparticle toxicity as resting T cells display a relative resistance while cells stimulated through the T cell receptor and CD28 costimulatory pathway show greater toxicity in direct relation to the level of activation. Mechanisms of toxicity appear to involve the generation of reactive oxygen species (ROS) with cancerous T cells producing higher inducible levels than normal T cells. In addition, nanoparticles were found to induce apoptosis and the inhibition of ROS was found to be protective against nanoparticle induced cell death. The novel findings of cell selective toxicity towards potential disease causing cells indicate a potential utility of ZnO nanoparticle in the treatment of cancer and/or autoimmunity.

DESCRIPTION OF THE PREFERRED EMBODIMENTS

Materials and Methods

1. Preparation and Characterization of Zinc Oxide Nanoparticles

ZnO nanoparticles were synthesized in diethylene glycol (DEG) by forced hydrolysis of zinc acetate at 160° C. as previously described and size control achieved by optimizing the hydrolysis ratio. The ZnO NPs were separated from DEG via centrifugation (15,000 rpm), washed with ethanol several times and dried to obtain a nanoscale powder sample. The ZnO chemical phase, crystallite size (8-13 nm) and shape were confirmed using x-ray diffraction (XRD), transmission electron microscopy (TEM) and spectrophotometry. The nanoparticles were then reconstituted in phosphate buffered saline (PBS) solution. After reconstitution, NPs were sonicated for 10 min and immediately vortexed before addition to cell cultures.

In order to aid in the investigations, additional FITC encapsulated ZnO (FITC-ZnO) particles were synthesized by forced hydrolysis and condensation of FITC-binding silane and silicate to obtain the FITC-SiO$_2$ core (Burns A, Ow H, and Wiesner U 2006 Fluorescent core-shell silica nanoparticles: towards "Lab on a Particle" architectures for nanobiotechnology. *Chem. Soc Rev.* 35 1028-1042) and then the ZnO surface layer formed using zinc salt as described previously Wang H, Wingett D, Engelhard M H, Feris K, Reddy K M, Turner P et al 2008 Fluorescent dye encapsulated ZnO particles with cell-specific toxicity for cancer treatment and biomedical applications submitted to *J Material Science: Materials in Medicine*. The core-shell structure of the ~200 nm sized FITC-ZnO particles and the presence of a surface layer of 8-13 nm sized ZnO nanoparticles were confirmed using TEM, XRD and x-ray photoelectron spectroscopy (XPS) studies, and fluorescence properties were investigated using photoluminescence spectroscopy and flow cytometry, as reported previously.

2. Isolation of CD4$^+$ T Lymphocytes and Cell Culture

Written, informed consent was obtained from all blood donors and the University Institutional Review Board approved the study. Peripheral blood mononuclear cells (PBMC) were obtained by Ficoll-Hypaque (Histopaque-1077, Sigma, St. Louis, Mo.) gradient centrifugation using heparinized phlebotomy samples. Cells were washed 3 times with Hank's buffer (Sigma) and incubated at $1 \times 10^6$ cells/mL in RPMI-1640 (Sigma) containing 10% fetal bovine serum (FBS). CD4$^+$ cells were obtained by negative immunonmagnetic selection per manufacturer's instructions using a cocktail of antibodies against CD45RO, CD8, CD19, CD14, CD16, CD56, CD8, and glycophorin A (StemCell Technologies, Vancouver, B.C.) with collection of unlabeled T cells (typically >96% CD4$^+$ and >90% viable as assessed by flow cytometry). Purified CD4$^+$ cells were cultured in RPMI/10% FBS at $1 \times 10^6$ cells/ml in 200 μL total volume in 96-well microtiter plates. The Jurkat and Hut-78 T cell lines (ATTC, Rockville, Md.) were cultured in RPMI 1640 supplemented with 10% FBS (Jurkat) or 20% FBS (Hut-78) and 2 mM L-glutamine, 1.5 g/L sodium bicarbonate, 4.5 g/L glucose, 10 mM HEPES, and 1.0 mM sodium pyruvate. Cells were maintained in log phase at 37° C. and 5% CO$_2$ and seeded at $1 \times 10^5$ cells/well in 96-well plates for individual experiments. To prevent overgrowth in co-culture experiments, Jurkat cells were seeded at $5 \times 10^4$ cells/well and primary T cells were seeded at $1 \times 10^5$ cells into the same well.

3. T-Cell Activation

For indicated experiments, primary human T cells were activated using immobilized CD3 antibody (1.0 μg/well of clone OKT3, ATCC, Rockville, Md.) +/–CD28 antibody (0.25 μg/well of clone CD28.2, PharMingen, San Diego, Calif.) in 96-well tissue culture plates. Cultures were treated with freshly prepared and sonicated NP for varying lengths of time and flow cytometry used to assess T cell viability via staining with propidium iodide (PI: BD Biosciences). T cell activation was verified by detecting an increase in membrane CD40L protein expression using flow cytometry.

4. Cell Viability and Flow Cytometry Staining

Methods of immunofluorescent staining and flow cytometry were performed as previously described. Briefly, cells were stained with fluorescently labeled antibodies (Beckman Coulter, Miami, Fla.) for 30 minutes at 4° C., washed two times, and immediately analyzed on a 3-color Epics flow cytometer (Beckman Coulter). Five to ten thousand events gated on size (forward scatter-FS) and granularity (side scatter-SSC) were analyzed, and expression of the percentage of positively staining cells or the mean fluorescence intensity (MFI) was determined by comparisons to isotype controls. Appropriate concentrations of each antibody were determined by titration for optimal staining prior to experimental use.

To assess cell viability, two different assays were employed. In the first assay, T cells were dually stained with fluoroscein isothiocyanate labeled antibodies (anti-CD4 for primary T cells and anti-HLA ABC for T cancer cell lines) followed by treatment with 50 μg/mL propidium iodide (PI) to monitor losses in membrane integrity. After 10 min of PI staining, fluorescent CountBright counting beads (Invitrogen, Carlsbad, Calif.) were added to samples to enable determinations of absolute cell numbers, and changes in PI staining used to quantify cell death. Nanoparticles were excluded from analysis based on absence of fluorescence signal and light forward scatter (FS) and side scatter (SSC) characteristics. A second viability assay, the LIVE/DEAD viability assay for mammalian cells (Invitrogen, Eugene, Oreg.) was used to verify results. Per manufacturer's protocol for flow cytometry, cells were dually stained with two fluorescently labeled probes that enable the simultaneous determination of live and dead cells in a sample. Calcein AM was used to stain live cells as it fluoresces only when cleaved by intracellular esterases and EthD-1 was used to identify dead/dying cells as it exclusively enters cells with disrupted cell membranes.

In co-culture experiments, Jurkat cells and primary T cells were distinguished from each other using differential gating based on their differing and non-overlapping light scattering properties indicative of size (FS) and granularity (SSC) between the two cell types. FS and SSC of Jurkat cells was ~2.2 and 3.2 times greater than for primary T cells, respectively.

5. ROS Production

To assay for reactive oxygen species (ROS) production, primary human T cells were treated with the oxidation-sensitive dye, 2', 7'-dichlorofluorescein diacetate (DCFH-DA; Invitrogen, Carlsbad, Calif.). The oxidation product of DCFH-DA has an excitation/emission maxima of ~495 nm/529 nm enabling detection using standard flow cytometry. Whole blood was treated with an ammonium chloride solution (1.5 M NH$_4$Cl, 0.1 M NaHCO$_3$, 0.01 M EDTA) to lyse red blood cells and centrifuged for 10 min at 4° C. to remove erythrocytic debris. The white blood cells were then resuspended in phenol red-free RPMI a $1 \times 10^6$ cells/mL and treated with 13 nm ZnO NP. After 18 h of treatment, cultures were loaded with 5 μM of DCFH-DA for 20 min and ROS production evaluated using flow cytometry as previously described. To ensure cells were capable of ROS production, control samples were activated with 25 ng/mL of PMA for 1 h after loading with DCFH-DA. White blood cell populations (i.e. T lymphocytes and monocytes) were distinguished by FS and SSC characteristics and staining with fluorescently-labeled antibodies (e.g. CD3, CD14). ROS production was also performed in Hut-78 cells using similar methodology.

6. ROS Quenching

To determine the role of ROS in NP-induced cell death, Jurkat leukemia cells were seeded in a 96-well plate at 0.2 mL per well at a concentration of $5 \times 10^5$ cells/mL. A stock solution of N-Acetyl Cysteine (NAC, Sigma Aldrich) was made in sterile nanopure water and added to cells at 5 mM or 10 mM for 1 h. After NAC pretreatment, cells were cultured with 0.3-0.5 mM ZnO NP for 24 h. Viability was determined by PI exclusion and flow cytometry with fluorescent CountBright counting beads (Invitrogen, Carlsbad, Calif.) added to samples to enable determination of absolute cell numbers.

7. Detection of Apoplosis

Mechanisms of ZnO NP induced cytotoxicity was evaluated by confocal microscopy using two different staining techniques; acridine orange and Vybrant® Apoptosis Assay Kit #2—AlexaFluor® annexin V/propidium iodide by Invitrogen (Eugene, Oreg.). Acridine orange stains double stranded DNA and allows for visualization of nuclear morphology. Invitrogen's Vybrant annexin V assay makes use of two different fluorescently labeled probes, annexin V and PI, to differentiate between live, necrotic and apoptotic cells. Briefly, Jurkat T cells were suspended in complete RPMI-1640 medium and plated at $5 \times 10^5$ on poly-d lysine coated glass bottom culture dishes (P35GC-1.5 mm-14 mm-C) supplied by MatTek Corporation (Ashland, Mass.). Samples were left untreated, treated with 0.3 mM ZnO NP, or with 100 nM okadaic acid as a positive control for apoptosis. Following a 20 h incubation at 37° C. (5% $CO_2$), cells were washed and stained with annexin V antibody/PI per manufacturer's protocol or stained with 5 µg/mL acridine orange for 10 min at 37° C., followed by washing and resuspension in PBS. Cells were visualized using a Zeiss LSM 510 META laser scanning confocal microscope (Zeiss, Germany). Images were acquired using factory-set dichronics (an argon laser set and two helium neon lasers) with either a 63× Plan Apochromat 1.4 oil DIC or 100× Plan Fluar 14.5 oil objective. Image acquisition and processing was performed using the LSM 510 META software.

8. Statistical Analyses

All data was analyzed using SAS, Inc. software (Cary, N.C.). Data for FIGS. 1, 3A, and 4 were analyzed using repeated measures of valiance with post hoc comparisons and significance levels defined as p<0.05. Repeated measures of variance analyses were used when two or more measurements of the same type were made on the same subject to determine statistical differences between the means and allow within-subject variation to be separated from between-subject variation. Data for FIGS. 3B and 7 were analyzed using a two-way analysis of variance (ANOVA) to test for statistical significance of the model and post hoc comparisons were used to test for statistically significant effects of treatment on cell viability (p<0.05).

Results

1. Activated T Cells are Preferentially Killed by ZnO NP

Previous studies from our laboratory have determined that toxicity of ZnO NP occurs in a cell dependent manner. For example, both gram negative and gram positive bacteria are killed at substantially lower ZnO NP concentrations than human T cells. To determine if differential toxicity to ZnO NP is dependent upon the microenvironment or signaling status of cell, toxicity effects were determined in resting primary human T cells and compared to cells activated through the T cell receptor (TCR). Normal peripheral blood CD4$^+$ T cells were isolated using negative immunomagnetic selection and either activated with stimulatory TCR antibodies (anti-CD3), costimulated with anti-CD3/anti-CD28, or left unactivated. The effects of ZnO NP on plasma membrane damage was assessed using propidium iodide (PI), a red fluorescent nuclear stain that enters only cells with disrupted plasma membranes.

Figure 1:
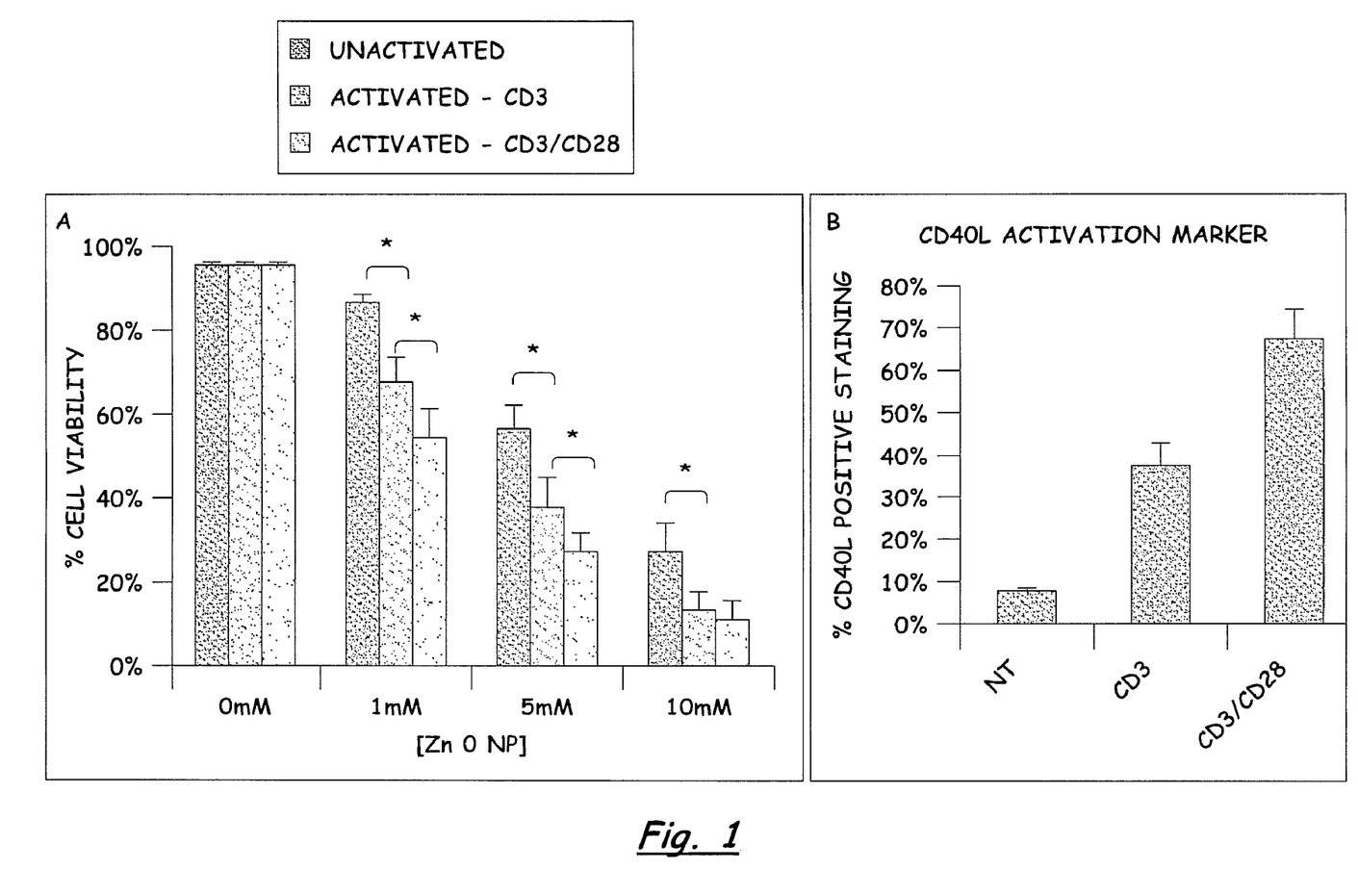
FIG. 1 is two charts about ZnO NP toxicity on unactivated verses activated primary human $CD4^+$ T cells.

According to FIG. 1, ZnO NP toxicity on unactivated versus activated primary human CD4$^+$ T cells. A) Human peripheral blood CD4$^+$ T cells were isolated (purity >95%) and activated with anti-CD3 antibodies, a combination of anti-CD3 and anti-CD28, or left unactivated. Cultures were concurrently treated with varying concentrations of ZnO NP for 22-24 h and cell viability determined using flow cytometry and PI uptake (means±standard error, n=6). Statistical analysis was performed using repeated measures analysis of variance and model based means post hoc test (p<0.05) with an asterisk denoting statistical significance. B) Verification of T cell activation was determined by concurrently monitoring expression of membrane CD40L protein using flow cytometry (means±standard error, n=5). As shown in FIG. 1A, the toxicity of ZnO NP to T cells is dependent on the activation state of the cell. Resting T cells displayed the most resistance to ZnO NP, with an $IC_{50}$ of ~5.9 mM. The inactivated status of these cells was verified by their lack of appreciable CD40L protein expression, a sensitive marker of T cell activation (FIG. 1B). Conversely, T cells partially activated by stimulation thorough the TCR pathway alone displayed significantly greater sensitivity to ZnO NP at all concentrations tested (p=0.0007 for control vs. CD3 at 1 mM, p=0.0009 at 5 mM and p=0.0052 at 10 mM NP). The partial activation status of these cells was verified by 38%±6.2% of the cells expressing membrane CD40L. Importantly, T cells activated through both the TCR and CD28 costimulatory pathway showed an even greater sensitivity to ZnO NP toxicity (e.g. 55% viability in CD3/CD28 activated vs. 69% in CD3 activated cells at 1 mM) which significantly differed from CD3 activated cultures at both 1 mM (p=0.0044) and 5 mM NP (p=0.0246) concentrations. Staining for membrane CD40L expression was used to confirm a greater extent of T cell activation in CD3/CD28 activated cultures (67%±7.0% cells staining positive for membrane CD40L). Control experiments using bulk micron sized ZnO powder or NP-free supernatant showed no appreciable toxicity effect at any of the concentrations tested (viability with bulk ZnO: 95±0.5% at 0 mM, 96±3% at 1 mM, 91±3% at 5 mM, 91±1% at 10 mM; 98% viability with NP-free supernatant equivalent to 1-10 mM) consistent with our previous observations.

In addition to PI uptake associated with disruption of membrane integrity, cell death following ZnO NP treatment was also supported by an increase (~17%; MFI change of 48 to 56) in light side scatter characteristics which is indicative of increased cellular granularity and a concurrent decrease (~8%; MFI change of 156 to 144) in forward scatter which reflects a decrease in cellular size at 10 mM NP concentrations that induce ~60% cell death. These results demonstrate that significantly more cell death is observed in activated T cells compared to resting cells over a relatively large range of NP concentrations tested (1-10 mM), and toxicity varies with the extent of T cell activation.

2. ZnO NP Preferentially Associate with Activated T Cells

To gain insights into mechanisms of differential cell toxicity, experiments were performed to determine whether NP preferentially associate with activated T cells compared to resting T cells. FITC-encapsulated ZnO NP (FITC-ZnO-NP) were prepared as described and their fluorescence properties used to monitor cell uptake/association. Primary CD4$^+$ T cells were either left unactivated or activated with CD3/CD28 antibodies and treated with 5 mM FITC-ZnO-NP for 4 h. Dual color flow cytometry was used to analyze changes in the FITC-NP signal on gated CD4$^+$ T cells.

Figure 2:
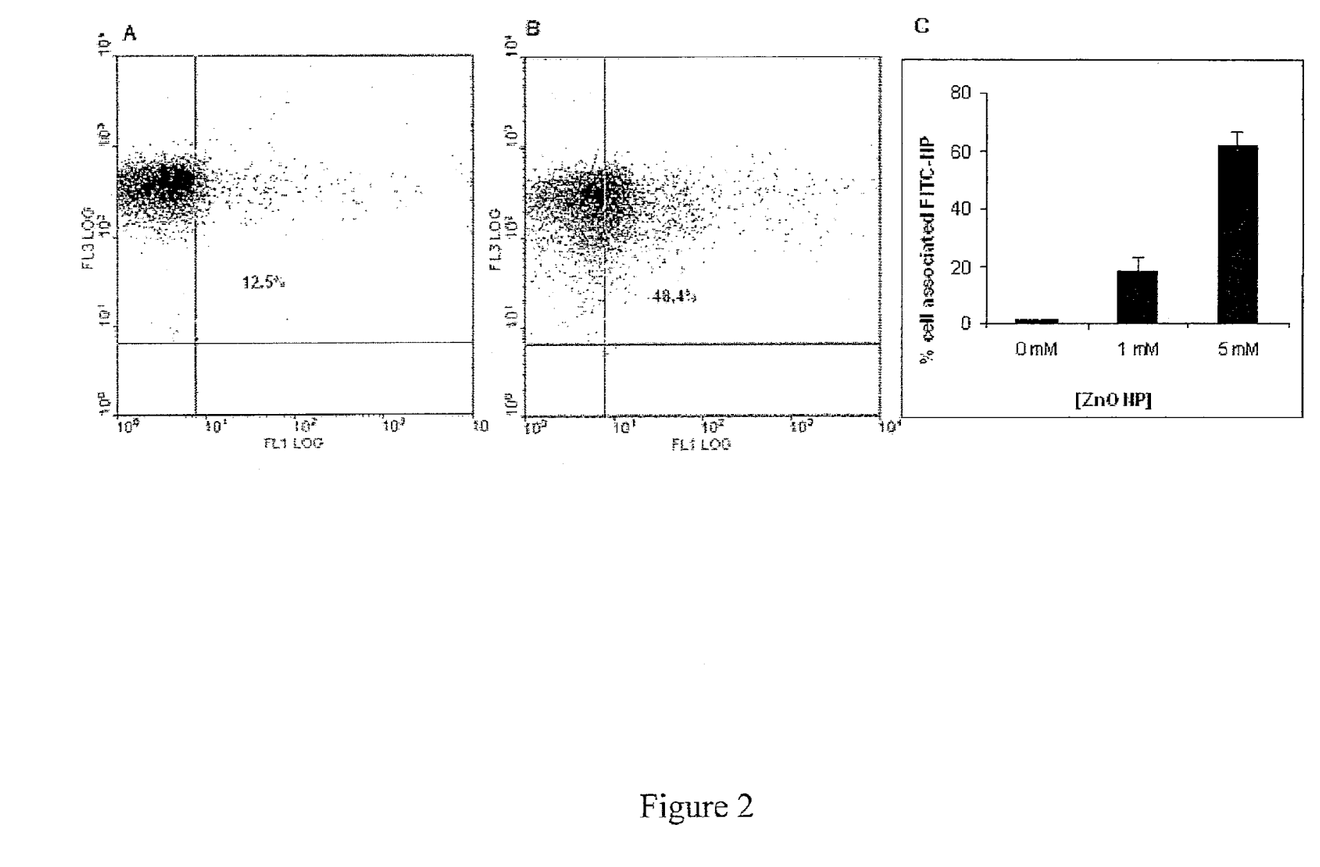
FIG. 2 is three charts about the activation of T cells promoting NP association.

According to FIG. 2, the activation of T cells promotes NP association. Primary CD4$^+$ T cells (>96% purity) were left untreated or activated with immobilized CD3/CD28 antibodies and cultures concurrently treated with 5 mM FITC encapsulated ZnO NP for 4 h. Cells were stained using an ECD-labeled CD4 Ab. Using flow cytometry, 10,000 events gated on CD4$^+$ cells were analyzed for changes in FITC fluorescence. Data from a representative histogram is presented with panel A) showing resting T cells cultured with FITC encapsulated NP and panel B) showing activated T cells cultured with FITC encapsulated NP. Inset numbers depict the percentage of FITC positive cells. The positioning of the quadrant on the x-axis was determined using T cells cultured without fluorescently labeled NP and set so 1% of cells appeared in quadrant 2. C) depicts a dose-dependent increase in NP association with T cells, n=3 with error bars depicting standard error. As shown in FIG. 2, resting T cells had a low NP associated fluorescence signal (12.5% FITC positive) while a substantially greater FITC signal (48.4% positive) was observed for activated T cells. A dose-dependent uptake of FITC-ZnO-NP was noted with greater NP association at 5 mM compared to 1 mM concentrations (~3.3 greater attachment at 5 mM; FIG. 2C). At the early time points evaluated in these studies, NP labeling did not appear to reflect a generalized increase in membrane permeability as no PI uptake indicative of cytotoxicity was observed following 4 h of exposure with 5 mM FITC-ZnO-NP. However, the expected loss of cell viability (73%±7.3% sue., n=3 with 1.25 mM) was detected upon extended 24 h exposure indicating that FITC-ZnO-NP behave similarly to unlabeled ZnO NP. In addition, our recent confocal microscopic studies have demonstrated FITC-ZnO-NP uptake and intracellular localization by human T cells. Collectively, these results indicate that the cellular processes accompanying T cell activation (eg. increased membrane protein expression, cell cycle progression) result in changes that promote strong physical interactions and consequent intracellular uptake of NP.

3. Preferential Killing of Cancerous Cells by ZnO NP

Given that differential ZnO NP toxicity exists between quiescent T cells and those activated with specific signals to trigger proliferation (FIG. 1), experiments were performed to determine whether continuously dividing cancer cells display an even greater sensitivity to ZnO NP toxicity. Jurkat leukemic and Hut-78 lymphoma T cell lines were treated with ZnO NP for 24 h and viability was determined by PI uptake. Both T cell cancer lines displayed strikingly greater (28-35 fold) sensitivity to NP toxicity compared to resting normal T cells (FIG. 3).

Figure 3:
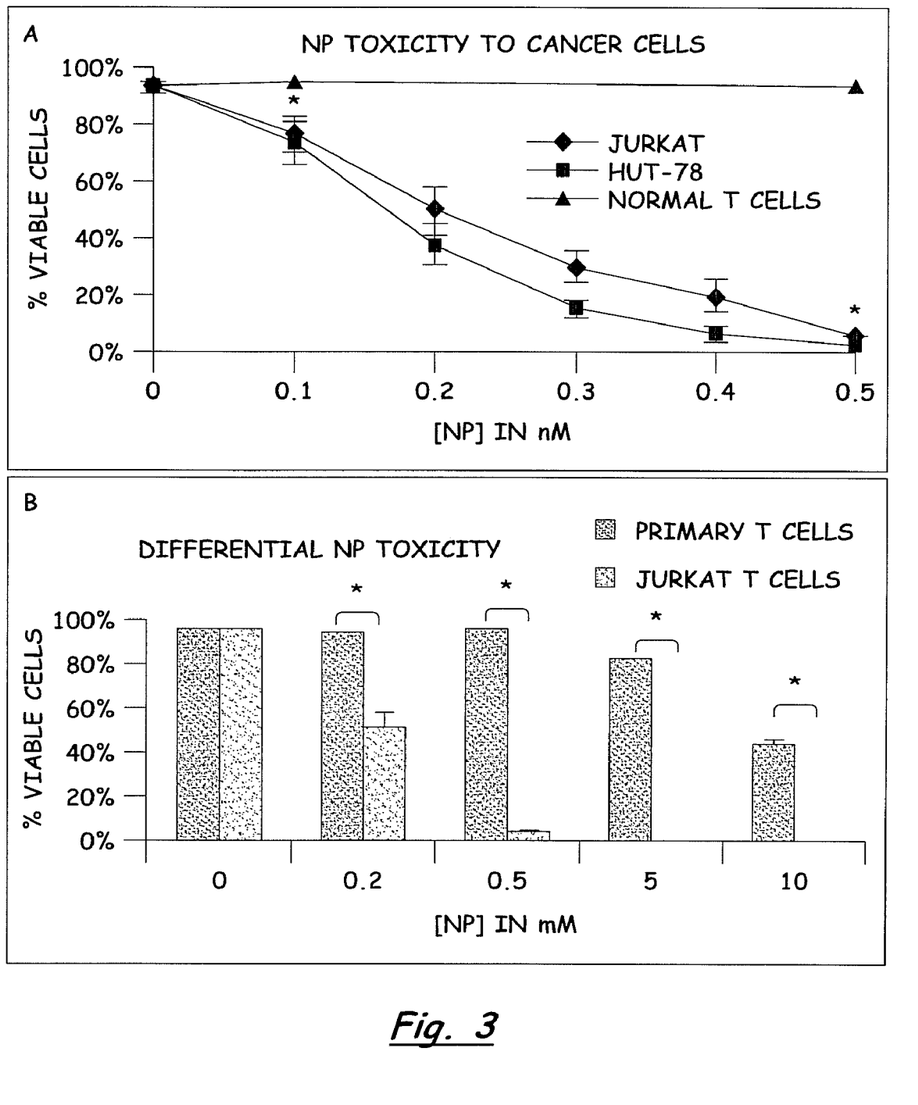
FIG. 3 is two charts about differential cytotoxic effects of ZnO NP on cancerous T cell lines and primary T cells.

According to FIG. 3, differential cytotoxic effects of ZnO NP on cancerous T cell lines and primary T cells. A) Jurkat, Hut-78 T cell lines, or normal primary T cells were treated with varying concentrations of ZnO nanopaiticles for 22-24 h and viability determined by monitoring PI uptake using flow cytometry as described for FIG. 1. Data from seven (Jurkat), three (Hut-78), and four (normal CD4$^+$ T cells) independent experiments is presented and error bars depict standard error. Data was analyzed using a repeated measures ANOVA and model based means post test. Statistical comparisons were made between each cancer cell line and primary T cells at 0.1 mM and 0.5 mM ZnO NP with significance levels defined as $p<0.05$ and indicated by an asterisk. B) Jurkat and primary T cell viability was assessed using the LIVE/DEAD® Viability/Cytotoxicity Kit for mammalian cells (Invitrogen, Eugene, Oreg.). Following ZnO NP exposure for 24 h, cells were stained with calcein AM (green fluorescence) and ethidium homodimer-1 (red fluorescence) to differentiate between live and dead cells, respectively. Data from a representative experiment is presented with error bars depicting standard error, n=3. A two-way analysis of variance combined with a model based means test indicates significant differences in viability between Jurkat and primary T cells for all NP concentrations tested (asterisk denotes $p<0.0001$). Significant differences were observed between Hut-78 and normal T cells ($p=0.0101$ and $0.0434$ at 1 mM and 5 mM NP, respectively) and Jurkat and normal T cells ($<0.0001$ at both 1 mM and 5 mM NP). An $IC_{50}$ of ~0.17 mM was observed for Hut-78 cells and ~0.21 mM for Jurkat T cells. No appreciable loss of primary T cell viability was observed at NP concentrations (e.g. 0.5 mM) that effectively killed the cancerous T cells.

To validate experimental results, a second viability assay was employed. Similar experiments were performed using the LIVE/DEAD viability assay (Invitrogen, Eugene, Oreg.) which allows for the simultaneous determination of live and dead cells in a sample by labeling live cells with the Calcein AM dye that fluoresces only when cleaved by intracellular esterase enzymes and the vital dye, EthD-1, which only enters dead/dying cells with disrupted cell membranes. As shown in FIG. 3B, nearly identical results were obtained using this independent assay for viability, with ZnO NP displaying preferential toxicity against cancerous cells compared to normal cells of identical lineage. It should be noted that no statistically significant change in primary T cell viability occurs between untreated control cells and cells treated with low NP concentrations (0.2 and 0.5 mM), while a significant decrease ($p<0.0001$) in Jurkat leukemia cell viability can readily be seen at the lowest concentration tested (~52% viable/48% dead at 0.2 mM) with no live cancer cells detectable at 5 mM NP.

To verify that preferential cancer cell killing occurs in the direct presence of normal healthy T cells, co-culture experiments were performed. For these experiments, Jurkat T cells were co-cultured with primary CD4$^+$ T cells, treated with various concentrations of ZnO NP for 24 h, and cell viability assessed by PI uptake.

Figure 4:
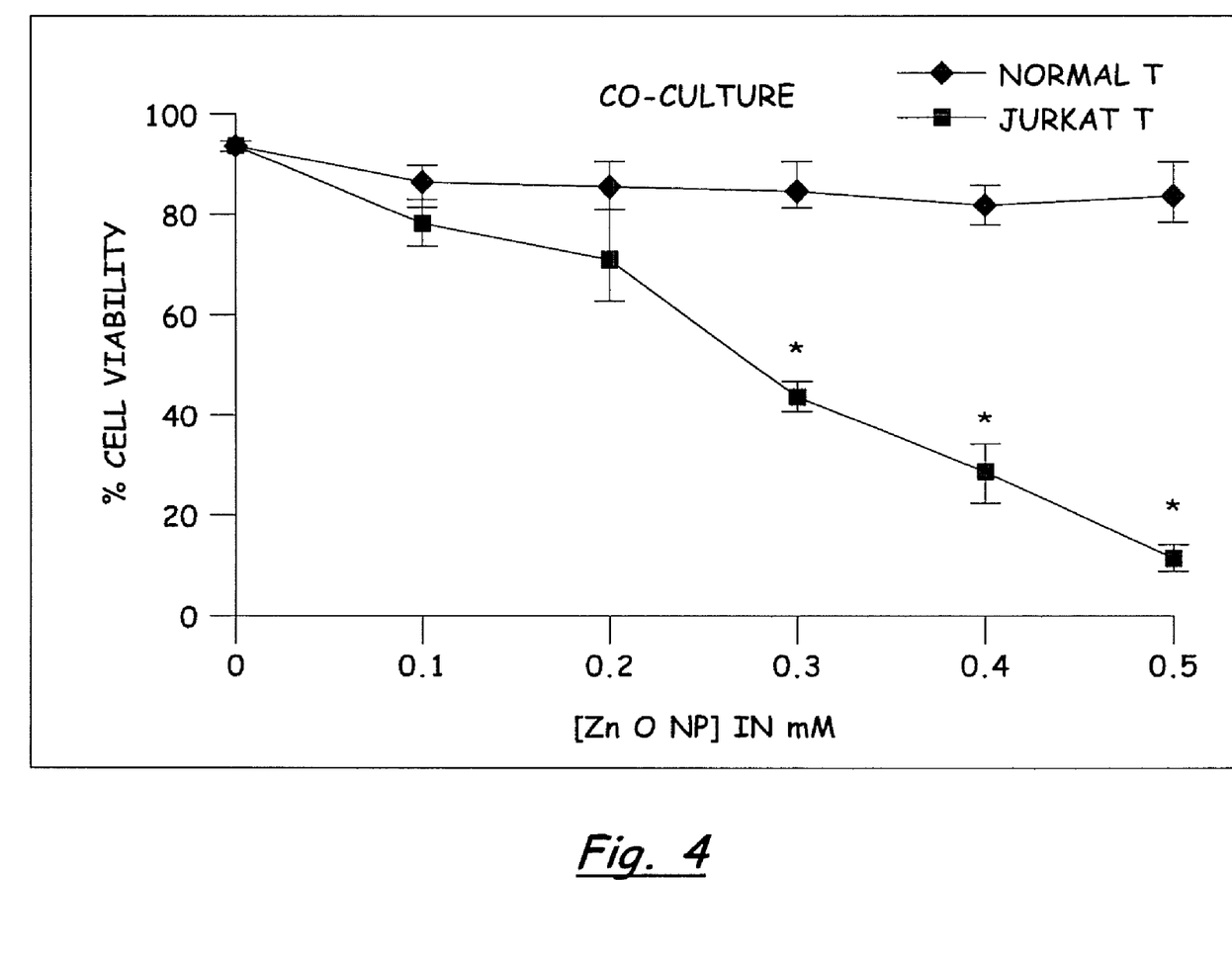
FIG. 4 is a chart about viability effects of ZnO NP on co-cultures of cancerous and normal T cells.

According to FIG. 4, viability effects of ZnO NP on co-cultures of cancerous and normal T cells. Individual wells in a 96-well plate were seeded with Jurkat and primary T cells and treated with various concentrations of ZnO nanopaiticles for 22-24 h. Viability was determined by monitoring PI uptake using flow cytometry. Data from three independent experiments is presented and error bars depict standard error. Statistical analysis was performed using a repeated measures ANOVA and model based means post hoc test. Significance levels were defined as $p<0.05$ and are indicated by an asterisk. FIG. 4 confirms the preferentially killing of cancerous Jurkat T cells with a very similar $IC_{50}$ value being observed for co-cultured Jurkat cells ($IC_{50}$ ~0.28 mM) compared to these cells cultured alone (FIG. 3). Again, only very limited cytotoxicity was observed on co-cultured normal T cells at corresponding NP concentrations with significant differences ($p<0.0001$) between cell types being observed at 0.3, 0.4, and 0.5 mM NP concentrations.

4. Kinetics of ZnO NP Mediated Toxicity

Additional experiments were performed to determine the kinetics of ZnO NP toxicity in both primary and cancerous T cells. Because primary and immortalized T cells have markedly different sensitivities to ZnO NP, concentrations were chosen for each cell type (10 mM for primary T cells and 0.5 mM for Jurkat T cells) that produce at least 75% cytotoxicity by 24 h exposure.

Figure 5:
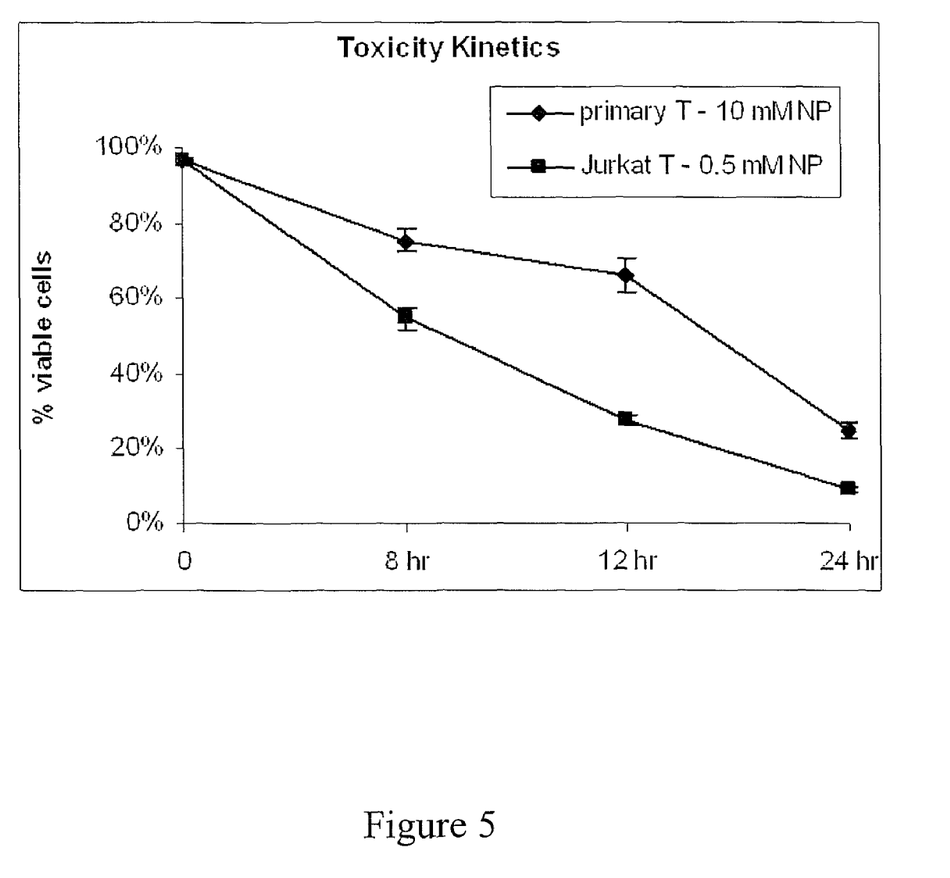
FIG. 5 is a chart about kinetics of ZnO NP toxicity on immortalized and primary human T cells.

According to FIG. 5, kinetics of ZnO NP toxicity on immortalized and primary human T cells. Freshly isolated CD4$^+$ T cells (purity >96%) were treated with 10 mM ZnO NP and Jurkat T cells were treated with 0.5 mM ZnO NP for varying times and viability determined using PI uptake and flow cytometry. Means±standard error from representative experiments are presented (n=3). As shown in FIG. 5, both primary T cells and Jurkat cells displayed similar kinetics with appreciable lose of cell viability beginning as early as 8 h post treatment and full toxicity effects requiring a longer treatment period of 24 h.

5. ZnO NP Induce ROS Production

Several types of nanomaterials including quantum dots and metal oxide NP have been shown to induce the generation of excess reactive oxygen species (ROS) resulting in modification and damage of cellular proteins, DNA, and lipids which can lead to cell death. To investigate oxidative stress produced by ZnO NP as a mechanism of cellular toxicity, experiments were performed using the cell permeable dye, DCFH-DA. In the presence of reactive oxygen species, including hydrogen peroxide and superoxide anion, DCFH-DA is oxidatively modified into a highly fluorescent derivative that is readily detectable using flow cytometry.

Figure 6:
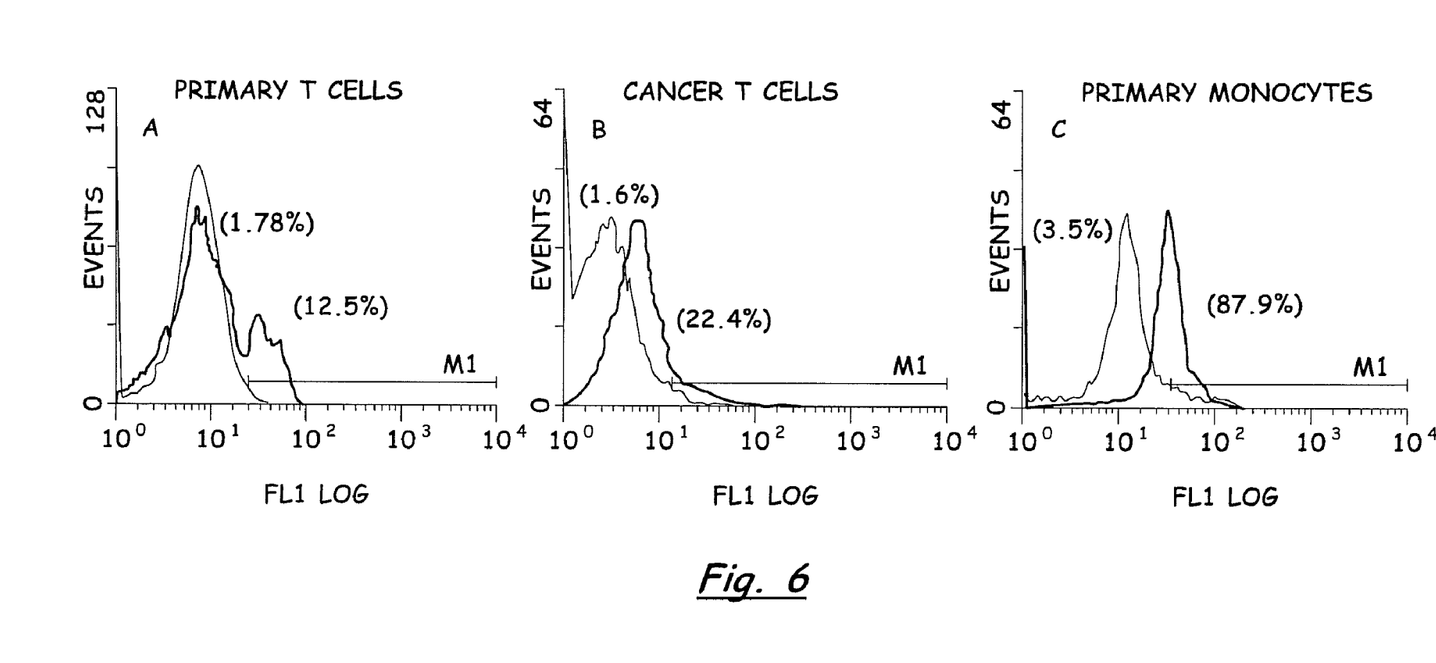
FIG. 6 is three charts about cellular production of ROS following ZnO NP exposure.

According to FIG. 6, cellular production of ROS following ZnO NP exposure. ROS generation was evaluated in primary T cells and monocytes and in the transformed Hut-78 T cell line following 18-24 h of ZnO NP exposure using the oxidation sensitive dye DCFH-DA and flow cytometry. A & C) Representative histograms depicting ROS production in primary T cells and monocytes. Assays were performed using freshly obtained whole blood in which red blood cells were removed following $NH_4Cl$ lysis. T lymphocytes and monocytes were gated based on staining with fluorescently labeled CD3 and CD14 antibodies and the oxidation product of DCFH-DA detected using the FL1 detector. B) Histogram depicting ROS production in the transformed Hut-78 T cell line. In each histogram, the light grey line depicts background fluorescence in DCFH-DA loaded cells while the black line depicts fluorescence in DCFH-DA loaded cells treated with ZnO NP for 18 h (A & C) or 24 h (B). To assess relative increases in ROS following NP treatment, a marker (M1) was set so that background fluorescent in control samples (DCFH-DA loaded/no NP) was between 1 and 3.5% and numbers in parentheses indicate the percentage of fluorescence positive cells. As shown in FIG. 6, a modest increase in DCF fluorescence was observed after 18 h of 5 mM ZnO NP exposure in primary lymphocytes (~7.0 fold increase—12.5/1.78) and an even stronger induction observed in Hut-78 T leukemic cells at 24 h (~14.0 fold increase). In addition, peripheral blood monocytes produced robust levels (~25.1 fold increase) of ROS following ZnO NP exposure consistent with the greater capacity of these cells for ROS generation. Increased ROS production was detectable as early at 8 h of NP exposure although greater levels were apparent at 18-24 h (data not shown). Because of the differing size and granularity properties of the cell types examined, different instrument voltage parameters were required which prevents direct comparisons of intrinsic levels of ROS between cell types.

6. Role of ROS in NP-Induced Cytotoxicity

Experiments were performed to determine if the T cell death that results from NP exposure is dependent on the generation of intracellular ROS. Jurkat cells were exposed to increasing concentrations of the antioxidant and ROS quencher, NAC (N-acetyl cysteine) prior to treatment with NP for 24 h.

Figure 7:
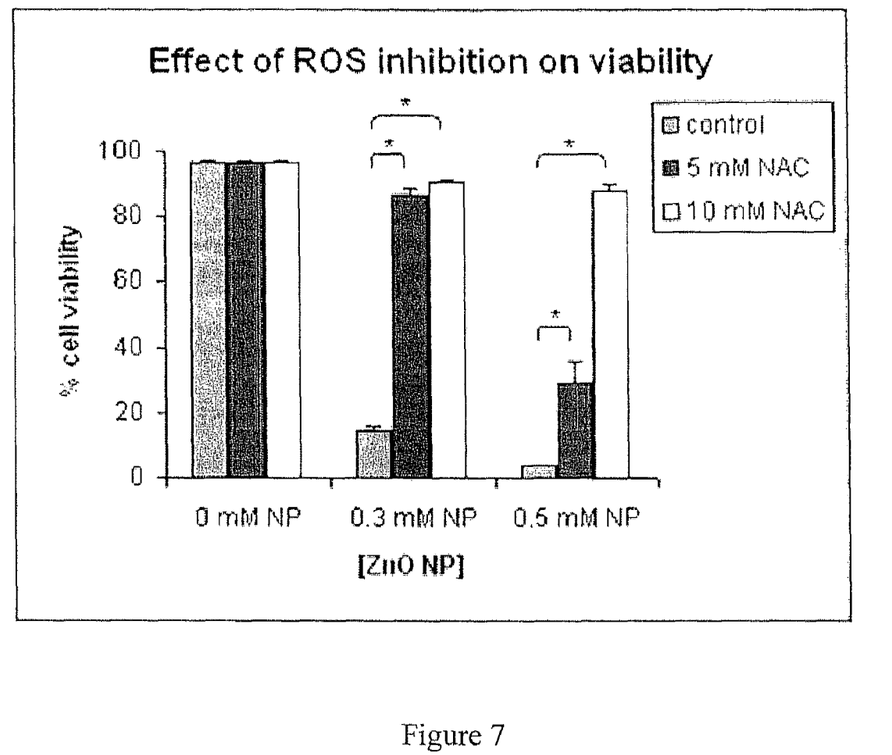
FIG. 7 is a chart about quenching of ROS protecting against NP-mediated cytotoxicity.

According to FIG. 7, quenching of ROS protects against NP-mediated cytotoxicity. Jurkat cells were pretreated with 5-10 mM N-acetyl cysteine for 60 min and then treated with 0.3-0.5 mM ZnO NP. After 24 h, cell viability was determined using propidium iodide exclusion and flow cytometry. Data from a representative experiment performed in triplicate is presented with error bars depicting standard error. A two way analysis of variance was performed followed by a model based means test to show significant differences in means of cell viability (%) between treatments (asterisk denotes $p<0.0001$). FIG. 7 shows that NAC has significant effects to prevent NP-induced cytotoxicity with rescue being observed at both NP concentrations tested. Significant differences ($p<0.0001$) were observed between cultures not pretreated with NAC and both NAC pretreatments (5 mM and 10 mM) for each NP concentration tested. For example, with 10 mM NAC, nearly 100% viability was retained even at an NP concentration previously shown to reduce cell viability below 10%. These results indicate that ROS generation plays a causal role in NP-induced cytotoxicity.

7. ZnO NP Induce Apoptosis

Experiments were performed to determine whether ZnO NP induce apoptosis or necrosis in T cells. Jurkat cells were treated with 0.3 mM NP for 20 h and apoptosis observed using two different experimental approaches. In the first assay, cells were stained with a green fluorescent annexin V antibody which reacts against externalized phosphatidylserine, a characteristic of apoptotic cells, and the red fluorescent propidium iodide dye which stains both late-stage apoptotic and necrotic cells displaying permeable membranes. As expected, viable control cells show only very weak staining with annexin V antibody and no detectable staining with PI (FIG. 8).

Figure 8:
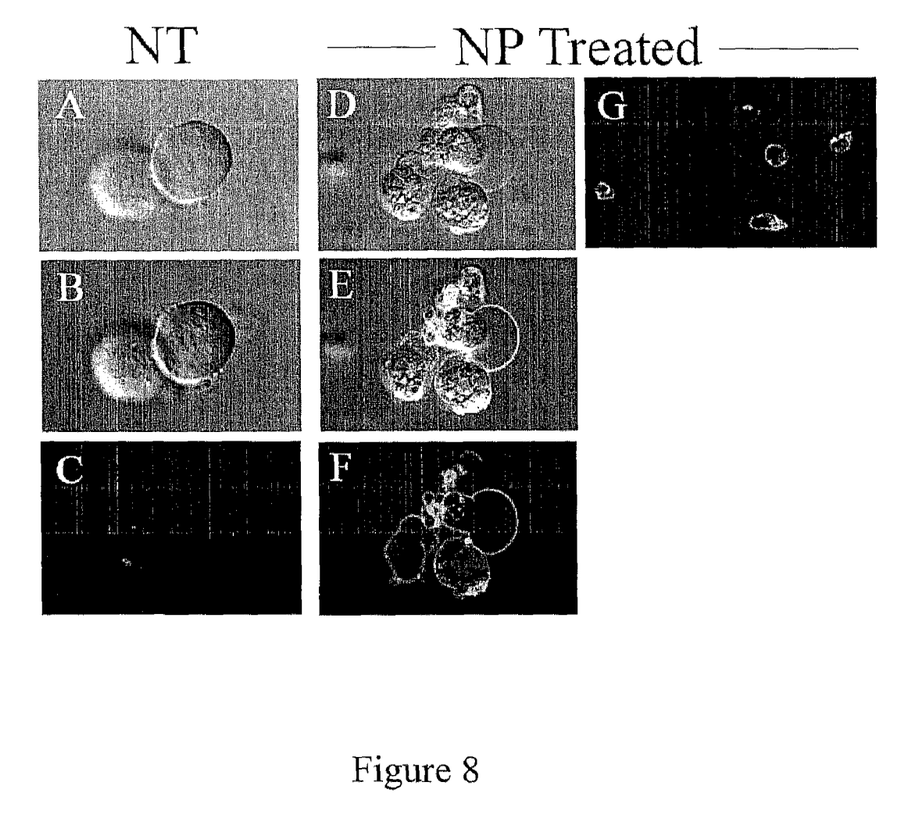
FIG. 8 is seven copies of photos about ZnO NP inducing apoptosis in Jurkat T cells.

According to FIG. 8, ZnO NP induce apoptosis in Jurkat T cells. Cells were left untreated, treated with 0.3 mM ZnO NP for 20 h, or treated with 100 nM okadaic acid for 20 h (positive control) and stained with a green fluorescent annexin V antibody to detect apoptotic membranes and the red fluorescent dye PI to detect permeable membranes using the Vybrant apoptosis assay kit #2 (Molecular Probes). Cells were visualized by confocal microscopy and representative images are shown. A-C) control cells not treated with NP; A) control differential interference contrast (DIC(image, B) control DIC image with green and red fluorescence overlay, C) control green and red fluorescence image. D-G) cells treated with NP; D) NP treated DIC image, E) NP treated DIC image with green and red fluorescence overly, F) NP treated green and red fluorescence image. G) an additional green and red fluorescence image of NP treated cells of lower magnification. Conversely, cells treated with ZnO NP stain positive with the apoptotic marker (eg. two out of the four cells in panel F and four out of five cells in panel G show green fluorescence only). Some dually stained were also observed as expected for late-stage apoptotic cells with permeable membranes. To further verify NP-induced apoptosis, similar cell cultures were stained with the DNA dye, acridine orange, which is used to detect apoptotic morphology characterized by nuclear fragmentation, cellular shrinkage, and chromatin condensation.

Figure 9:
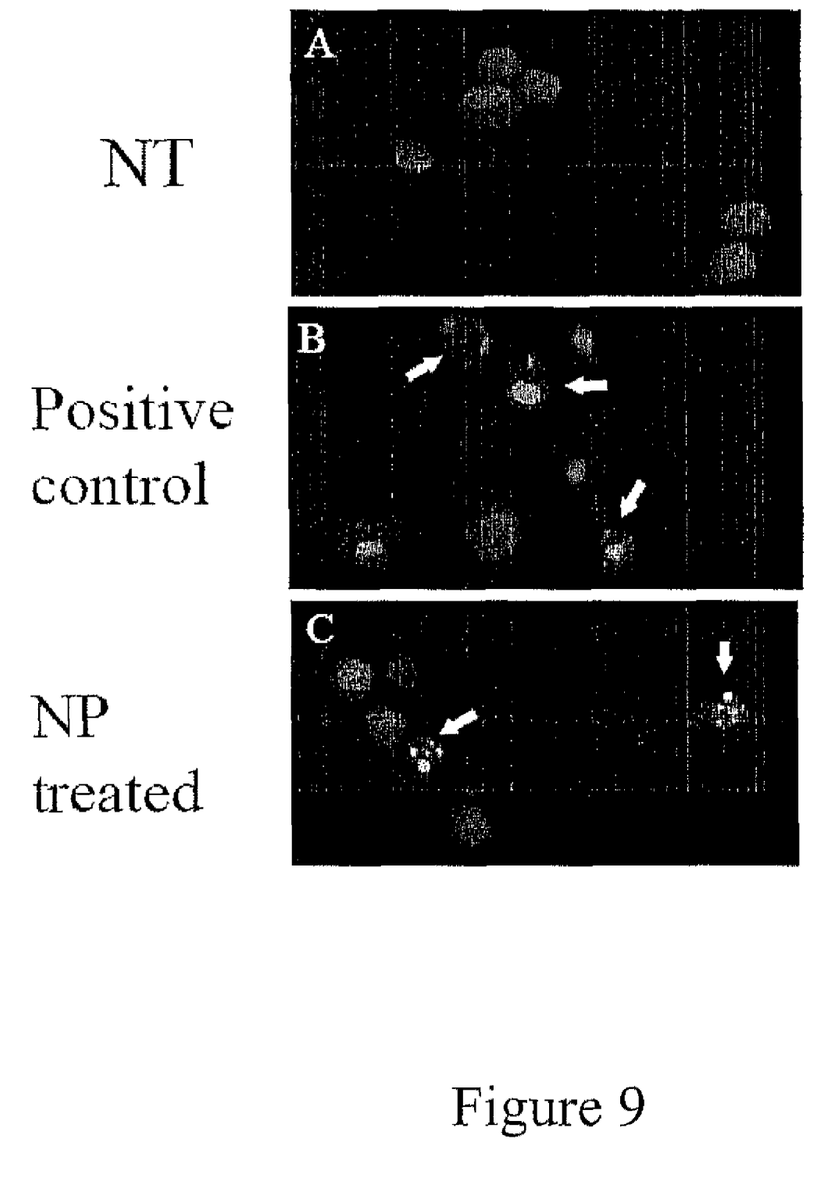
FIG. 9 is three copies of photos about detection of apoptotic morphological changes in Jurkat T cells treated with ZnO NP.

According to FIG. 9, detection of apoptotic morphological changes in Jurkat cells treated with ZnO NP. Cells were left untreated (A), or treated with 100 nM okadaic acid for 20 h as a positive control for apoptosis (B), or treated with 0.3 mM ZnO NP for 20 h (C) and stained with acridine orange and visualized by fluorescent microscopy. Arrows indicate typical apoptotic cells characterized by a shrunken appearance and condensed or fragmented nuclei. As shown in FIG. 9, these morphological changes were observed in NP treated cultures and cells treated with the apoptosis inducer okadaic acid, but not in control samples. Collectively, these results indicate that ZnO NP induce apoptosis in Jurkat T cells.

Discussion

In this study we examined the toxicity profiles of human primary cells and transformed tumor cells to ZnO NP. Because cellular response is dynamic and the ultimate phenotype is affected by a myriad of competing or overlapping signals present in the microenvironment, studies were performed to determine how ZnO NP affect quiescent cells compared to rapidly dividing tumor cells and whether different activation stimuli result in different toxicity responses. Here we present novel findings demonstrating that cancerous T cells are markedly more susceptible (~28-35 times) to ZnO NP mediated toxicity than their normal counterparts (FIG. 3). These findings may be of important clinical interest as one of the greatest challenges facing chemotherapy is the inability of anticancer drugs to effectively distinguish between normal and transformed tissue. Although many commonly used chemotherapeutic drugs target rapidly dividing cells, many suffer from a relatively low therapeutic index, that is, the ratio of toxic dose to effective dose. This limitation frequently causes a broad range of toxicities leading to dose limiting toxicity and a concomitant reduction in antitumor efficacy. Importantly, the preferential toxicity of ZnO NP towards cancerous T cells is of substantial magnitude, especially in comparison to ex vivo indices reported for other commonly used chemotherapeutic agents using similar cell viability assays. Therapeutic indices of $\leqq 10$ have been reported for both doxorubicin and carboplatin against a variety of tumors including acute myelogenous leukemia, non-Hodgkin's lymphoma, ovarian, and other solid tumors. Thus, the inherent differential toxicity of ZnO NP against rapidly dividing cancer cells raises exciting opportunities for their potential use as anticancer agents, and the selectivity of these nanomaterials can be expected to be even further enhanced by design by linking tumor targeting ligands such as monoclonal antibodies, peptides, and small molecules to tumor-associated proteins, or by using NP for drug delivery.

The preferential killing of rapidly dividing cancer cells relative to quiescent cells of the same lineage suggests that mechanisms of ZnO NP toxicity might be related to the proliferative potential of the cell. This hypothesis is further supported by studies comparing responses in healthy primary resting T cells to identical cultures in which cells were either activated thorough the T cell receptor signaling pathway or via both TCR and CD28 costimulation pathways (FIG. 1). Signal transduction through the TCR pathway is recognized as an essential event required for resting T cells to enter the cell cycle and proliferate. A second signal provided by ligation through the CD28 receptor protein augments TCR signaling and enables maximal T cell activation and proliferation. Thus, our findings revealing a spectrum of toxicity profiles that correlate with the activation status and proliferative capacity of the cell supports the hypothesis that ZnO NP preferentially target rapidly dividing cells. Quiescent T cells displayed the most resistance to ZnO NP while TCR stimulated cells had less resistance. Importantly, TCR/CD28 costimulated T cells were the most sensitive to ZnO NP toxicity and a greater cell association with fluorescently labeled ZnO NP was observed in activated T cells compared to quiescent T cells (FIG. 1). These findings indicate that the selective elimination of activated T cells may be feasible, when desired, such as in the treatment of auto immunity.

In a number of autoimmune diseases including multiple sclerosis and psoriasis, self-reactive T cells are a pathogenic subset underlying disease processes and exist in a predominately activated state as they are continually exposed to specific antigen present in normal body tissue. Because only a very small percentage of the total T cell repertoire are self-reactive and pathogenic in autoimmunity, the ability of identical concentrations of ZnO NP to preferentially induce cytotoxicity in self-reactive activated T cells while leaving the unactivated T cell repertoire largely intact and immunity uncompromised against future infections is an incredibly attractive approach which may ultimately become feasible. Based on data presented here, ZnO NP hold promise in this novel biomedical application, especially if their selectivity against self-reactive pathogenic cells can be improved by the covalent attachment of antibodies specific to proteins expressed predominantly on activated T cells such as CD40L and OX40.

A number of studies indicate that certain nanomaterials, including metal oxide NP, have the potential to exhibit spontaneous ROS production based on material composition and surface characteristics while other nanomaterials trigger ROS production only in the presence of select cell systems. Results from our flow cytometry experiments provide the first evidence of ROS production in a biotic environment following ZnO NP exposure. These findings have important implications regarding mechanisms of cellular toxicity as elevated ROS production that exceeds the capacity of the cellular antioxidant defense system causes cells to enter a state of oxidative stress which results in damage of cellular components such as lipids, proteins, and DNA. The oxidation of fatty acids then leads to the generation of lipid peroxides that initiate a chain reaction leading to disruption of plasma and organelle membranes and subsequent cell death. We observed a concentration and time dependent increase in ROS production in primary T cells following ZnO NP exposure (FIG. 6), with even higher levels being observed in monocytes consistent with the ability of these cells to generate large amounts of ROS during an immune response. Interestingly, immortalized T cells produced greater levels of ROS than primary T cells which may mechanistically underlie the greater susceptibility of cancerous T cells to NP-mediated toxicity. Indeed, studies using the ROS quencher, NAC, demonstrated the causal role of ROS generation in NP-mediated cytotoxicity (FIG. 7).

As there is increasing evidence that elevated ROS acts as a critical signaling molecule in the induction of apoptosis induced by many different stimuli, studies were performed to determine if NP induced cytotoxicity occurs via an apoptotic pathway. Results presented in FIGS. 8 and 9 provide strong evidence that ZnO NP induce apoptosis in cells of T lymphocyte lineage. Collectively, these studies indicate that a primary mechanism of ZnO NP cytotoxicity may precede by inducing the generation of ROS which then underlies the induction of apoptosis, a process that may be prevented by antioxidants and ROS quenchers. These observations may provide the basis for the development of new rational strategies to protect against NP toxicity or enhance the destruction of disease causing cell types such as cancer cells.

Conclusion

The key findings of this work support the view that ZnO NP induce toxicity in a cell-specific and proliferation dependent manner with rapidly dividing cells being the most susceptible and quiescent cells being the least sensitive. The marked difference in cytotoxic response between cancer cells and their normal counterparts, as well as differences between activated and resting T lymphocytes, suggests an exciting potential for ZnO NP as novel alternatives to cancer chemotherapy and radiation therapy as well as new approaches for treatment of autoimmunity.

Although this invention has been described above with reference to particular means, materials and embodiments, it is to be understood that the invention is not limited to these disclosed particulars, but extends instead to all equivalents within the scope of the following claims.

What we claim is:
1. A method of killing cancer cells, the method comprising:
providing a cancer cell in the presence of a healthy cell,
wherein the cancer cell is from leukemia and/or lymphoma;
contacting the cancer cell and the healthy cell with a ZnO nanoparticle, wherein the ZnO nanoparticle has a preferential association with the cancer cell over the healthy cell, and
wherein a targeting ligand is not associated with the ZnO nanoparticle; and
killing the cancer cell.

2. The method of claim 1, wherein the ZnO nanoparticle is at a concentration of about 0.1 mM to about 5 mM.

3. The method of claim 1, wherein the preferential association of the ZnO nanoparticle with the cancer cell comprises intracellular uptake of the ZnO nanoparticle.

4. The method of claim 1, wherein the ZnO nanoparticle kills the cancer cell via an apoptotic pathway.

5. The method of claim 4, wherein the apoptotic pathway is induced by a reactive oxygen species produced because of the presence of the ZnO nanoparticle.

6. The method of claim 1, wherein the ZnO nanoparticle induces the generation of reactive oxygen species within the cell.

7. A method of preferentially inducing apoptosis in activated T-cells over resting T-cells, the method comprising:
    providing an activated T-cell in the presence of a resting T-cell;
    contacting the activated T-cell and the resting T-cell with a ZnO nanoparticle,
        wherein the ZnO nanoparticle has a preferential association with the activated T-cell; and
    inducing apoptosis in the activated T-cell without exciting the ZnO nanoparticle with electromagnetic radiation.

8. The method of claim 7, wherein a targeting ligand is not associated with the ZnO nanoparticle.

9. The method of claim 7, wherein the ZnO nanoparticle is at a concentration of about 0.1 mM to about 5 mM.

10. The method of claim 7, wherein the preferential association of the ZnO nanoparticle with the activated T-cell comprises intracellular uptake of the ZnO nanoparticle.

11. The method of claim 7, wherein apoptosis is induced by a reactive oxygen species produced in the presence of the ZnO nanoparticle.

12. A method of treating auto immune disease, the method comprising:
    providing an activated T-cell in the presence of a normal body tissue,
        wherein the activated T-cell has become activated due to multiple sclerosis or psoriasis;
    contacting the activated T-cell with a ZnO nanoparticle,
        wherein the ZnO nanoparticle has a preferential association with the activated T-cell over the normal body tissue; and
    generating a reactive oxygen species within the activated T-cell at a greater concentration than in the normal body tissue.

13. The method of claim 12, wherein a targeting ligand is not associated with the ZnO nanoparticle.

14. The method of claim 12, wherein the ZnO nanoparticle is at a concentration of about 0.1 mM to about 5 mM.

15. The method of claim 12, wherein the preferential association of the ZnO nanoparticle with the activated T-cell comprises intracellular uptake of the ZnO nanoparticle.

16. The method of claim 12, wherein the reactive oxygen species induce apoptosis.

17. A method of treating cells exposed to a ZnO nanoparticle, the method comprising:
    providing a cell exposed to a ZnO nanoparticle; and
    contacting the cell with an antioxidant or a reactive oxygen species quencher.

18. The method of claim 17, wherein a targeting ligand is not associated with the ZnO nanoparticle.

19. The method of claim 17, wherein a targeting ligand is associated with the ZnO nanoparticle.

20. The method of claim 17, wherein the ZnO nanoparticle is internalized into the cell.

21. The method of claim 17, wherein the antioxidant or the active oxygen species quencher prevents the induction of apoptosis.

* * * * *